US009198620B2

(12) United States Patent
Balji et al.

(10) Patent No.: US 9,198,620 B2
(45) Date of Patent: Dec. 1, 2015

(54) CABLES FOR PATIENT MONITORING AND RELATED SYSTEMS WITH INTEGRATED FRONT END

(71) Applicant: Mindray DS USA, Inc., Mahwah, NJ (US)

(72) Inventors: Jack Balji, Mahwah, NJ (US); Cadathur Rajagopalan, Dumont, NJ (US); Scott Eaton, Briarcliff Manor, NY (US)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 14/452,410

(22) Filed: Aug. 5, 2014

(65) Prior Publication Data

US 2014/0350416 A1    Nov. 27, 2014

Related U.S. Application Data

(63) Continuation of application No. 12/645,304, filed on Dec. 22, 2009, now Pat. No. 8,797,714.

(51) Int. Cl.
*H02H 1/06*    (2006.01)
*A61B 5/00*    (2006.01)
*A61B 5/021*    (2006.01)
*A61B 5/0215*    (2006.01)
*A61B 5/03*    (2006.01)

(52) U.S. Cl.
CPC ............. *A61B 5/7225* (2013.01); *A61B 5/0002* (2013.01); *A61B 5/002* (2013.01); *A61B 5/021* (2013.01); *A61B 5/742* (2013.01); *A61B 5/0006* (2013.01); *A61B 5/02152* (2013.01); *A61B 5/031* (2013.01); *A61B 2562/222* (2013.01); *A61B 2562/227* (2013.01)

(58) Field of Classification Search
USPC ......................................................... 361/437
See application file for complete search history.

(56) References Cited

U.S. PATENT DOCUMENTS

| | | |
|---|---|---|
| 4,974,600 A | 12/1990 | Reyes |
| 5,135,002 A | 8/1992 | Kirchner et al. |
| 5,269,311 A | 12/1993 | Kirchner et al. |
| 5,341,812 A | 8/1994 | Allaire et al. |
| 5,368,041 A | 11/1994 | Shambroom |
| 5,381,804 A | 1/1995 | Shambroom |
| 5,566,680 A | 10/1996 | Urion et al. |
| 5,830,212 A | 11/1998 | Cartmell et al. |
| 5,871,451 A | 2/1999 | Unger et al. |
| 5,957,838 A | 9/1999 | Rantala |
| 6,142,949 A | 11/2000 | Ubby |
| 6,236,874 B1 | 5/2001 | Devlin et al. |
| 6,240,315 B1 * | 5/2001 | Mo et al. .......................... 607/41 |

(Continued)

OTHER PUBLICATIONS

Office Action mailed Jun. 27, 2011 in U.S. Appl. No. 12/432,558, filed Apr. 29, 2009.

(Continued)

*Primary Examiner* — Ronald W Leja
(74) *Attorney, Agent, or Firm* — Kory D. Christensen; Stoel Rives LLP

(57) ABSTRACT

Patient monitoring systems can include a system for transmitting information from a patient parameter sensor to a patient monitor. The system can include an analog-to-digital converter close to the patient parameter sensor and can transmit digital signals through a cable to the patient monitor.

19 Claims, 12 Drawing Sheets

(56) References Cited

U.S. PATENT DOCUMENTS

| | | |
|---|---|---|
| 6,654,631 B1 | 11/2003 | Sahai |
| 6,728,564 B2 | 4/2004 | Lahteenmaki |
| 6,850,788 B2 * | 2/2005 | Al-Ali ............ 600/323 |
| 6,891,379 B2 | 5/2005 | Kelly et al. |
| 7,112,097 B1 | 9/2006 | Lam |
| 7,272,428 B2 | 9/2007 | Hopman et al. |
| 7,344,500 B2 * | 3/2008 | Talbot et al. ............ 600/365 |
| 7,427,165 B2 * | 9/2008 | Benaron et al. ............ 385/75 |
| 7,933,642 B2 | 4/2011 | Istvan et al. |
| 8,109,883 B2 | 2/2012 | Meyer et al. |
| 8,115,101 B2 | 2/2012 | Balji et al. |
| 8,442,607 B2 | 5/2013 | Banet et al. |
| 8,475,370 B2 | 7/2013 | McCombie et al. |
| 8,797,714 B2 | 8/2014 | Balji et al. |
| 2002/0095074 A1 | 7/2002 | Al-Ali |
| 2004/0082866 A1 | 4/2004 | Mott et al. |
| 2004/0105245 A1 | 6/2004 | Kelly et al. |
| 2006/0047214 A1 | 3/2006 | Fraden |
| 2006/0073728 A1 | 4/2006 | Zaiken et al. |
| 2006/0286960 A1 * | 12/2006 | Goehler ............ 455/403 |
| 2006/0287589 A1 * | 12/2006 | Wobermin ........ A61B 5/0002 600/324 |
| 2007/0112274 A1 * | 5/2007 | Heitzmann ........ A61B 5/0002 600/485 |
| 2007/0287924 A1 | 12/2007 | Glocker et al. |
| 2009/0146062 A1 | 6/2009 | Russell |
| 2010/0276195 A1 | 11/2010 | Balji et al. |
| 2010/0277119 A1 | 11/2010 | Montague et al. |
| 2011/0019595 A1 * | 1/2011 | Magar ............ A61B 5/0002 370/279 |
| 2011/0152628 A1 | 6/2011 | Balji et al. |
| 2012/0130239 A1 | 5/2012 | Meyer et al. |
| 2012/0265077 A1 | 10/2012 | Gille et al. |
| 2012/0310081 A1 | 12/2012 | Adler et al. |
| 2013/0184638 A1 | 7/2013 | Scarpaci et al. |
| 2014/0275825 A1 * | 9/2014 | Lisogurski ........ A61B 5/0205 600/301 |

OTHER PUBLICATIONS

Notice of Allowance mailed Dec. 2, 2011 for U.S. Appl. No. 12/432,558, filed Apr. 29, 2009.

Office Action mailed Aug. 1, 2013 in U.S. Appl. No. 12/645,304, filed Dec. 22, 2009.

Final Office Action mailed Dec. 20, 2013 in U.S. Appl. No. 12/645,304, filed Dec. 22, 2009.

Notice of Allowance mailed Jun. 9, 2014 for U.S. Appl. No. 12/645,304, filed Dec. 22, 2009.

* cited by examiner

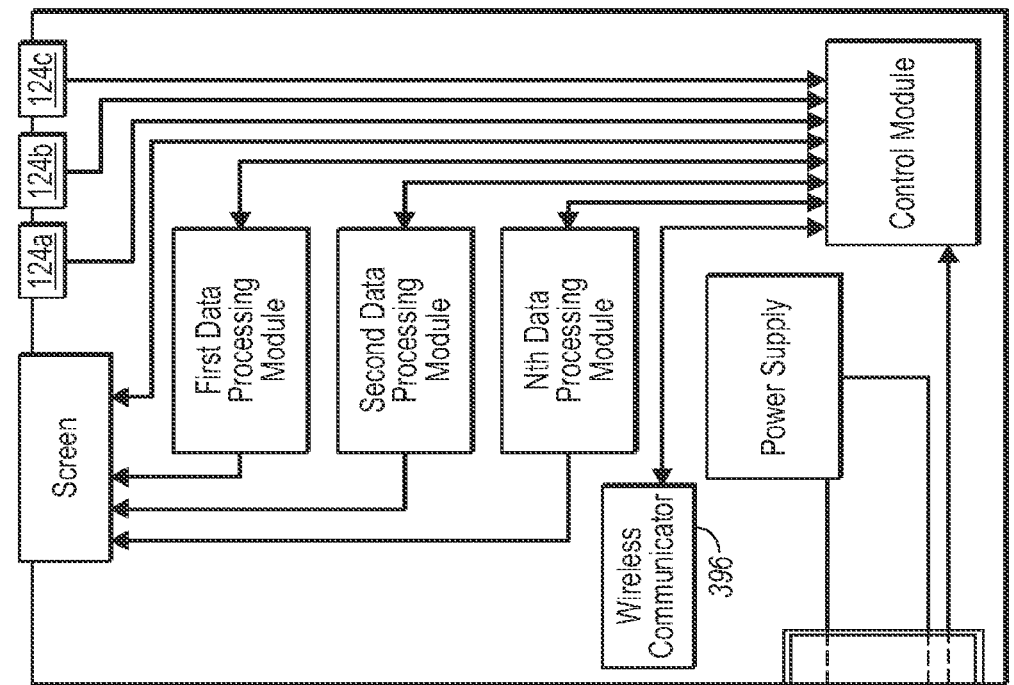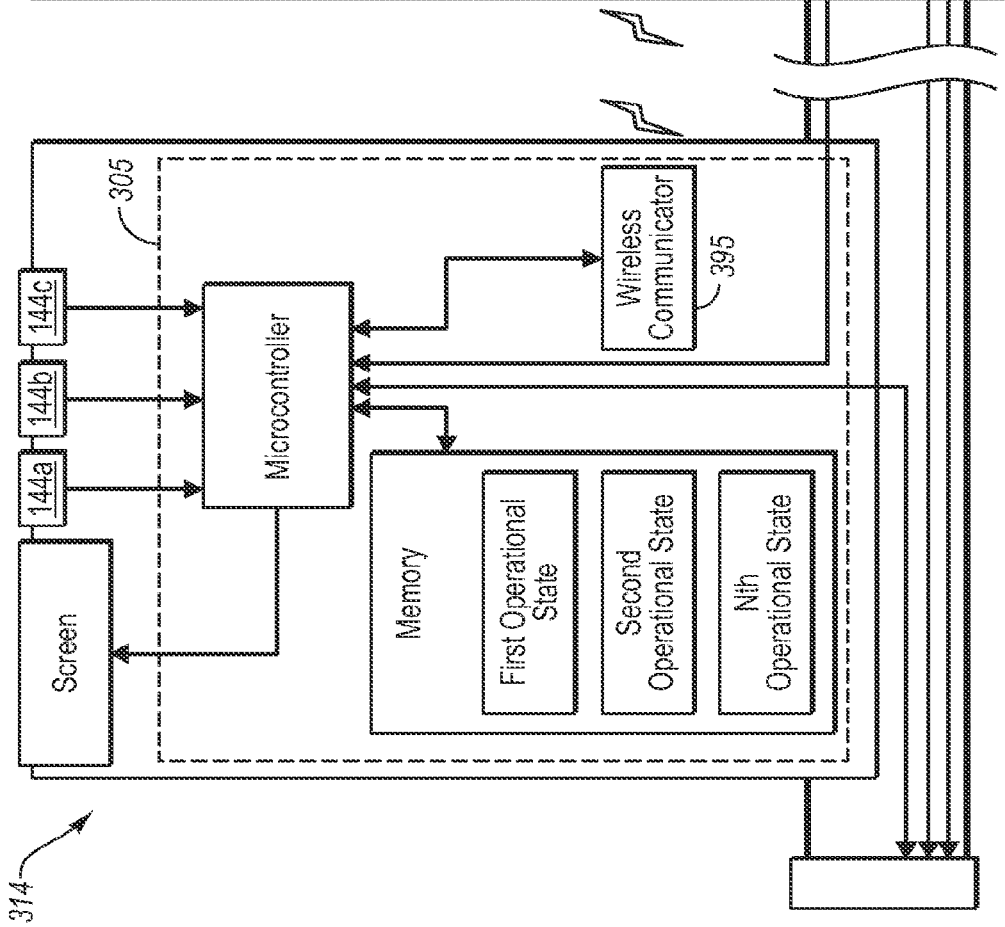
Fig. 3

CABLES FOR PATIENT MONITORING AND RELATED SYSTEMS WITH INTEGRATED FRONT END

TECHNICAL FIELD

The present disclosure relates to cables for use in monitoring patients.

SUMMARY

Embodiments of cables for use in monitoring patients, as well as related systems and methods, are disclosed.

BRIEF DESCRIPTION OF THE DRAWINGS

FIG. 3 is a simplified block diagram schematically illustrating other embodiments of a monitor, a cable, and control unit in a coupled state;

DETAILED DESCRIPTION

Figure 1:
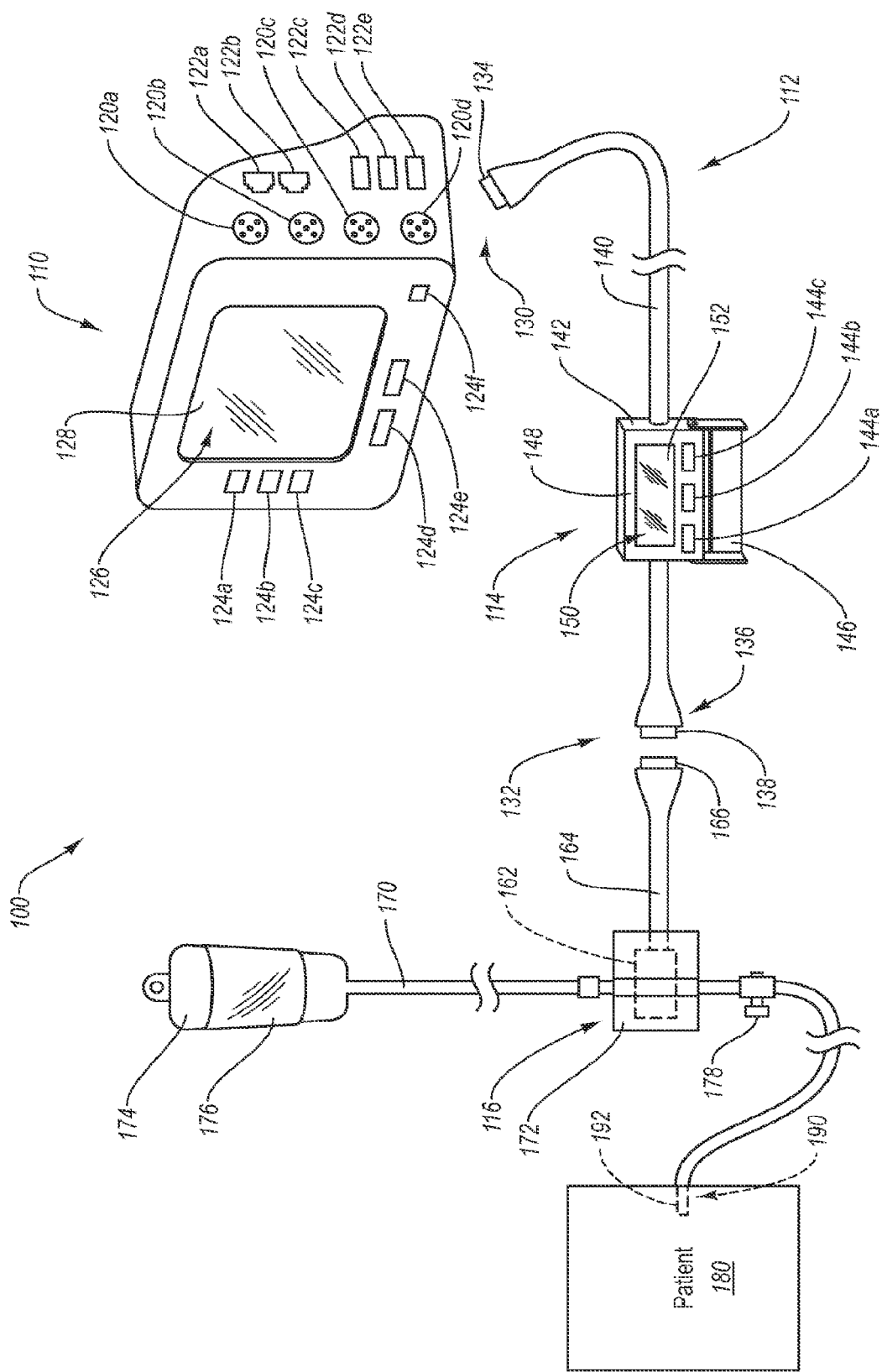
FIG. 1 is a partially exploded perspective view of an embodiment of a patient monitoring system including a monitor, cable, and control unit.

Devices for monitoring physiological or other parameters of a patient, such as the patient's blood pressure, cardiac activity, and/or temperature, generally receive information regarding the patient parameters via electrical cables that are connected to sensors positioned near, on, and/or inside the patient. Often, the patient may be transferred from one room of a hospital to another, such as from an emergency room to an intensive care unit or from a surgery room to a recovery room. In such instances, it can be desirable to disconnect the cables from one monitoring device and connect them to another. The standard practice for disconnecting and connecting cables in this manner requires a medical practitioner to ensure that each cable is routed from the sensor at or near the patient to the proper port of the new monitor. The cables often become intertwined or jumbled during use, thus this process can be time consuming and prone to errors. This can be problematic in the accuracy-sensitive and often time-sensitive context of patient monitoring.

Moreover, the electrical cables transmit analog signals from the sensors to the patient monitoring devices. In many cases, the cables can be relatively long such that the analog signals, which may have low amplitudes in any event, are attenuated. Moreover, the analog signals can be subject to interference, distortion, or other artifacts that can result from the distance the signals travel and/or from other sources, such as, for example, electromagnetic radiation from other devices or nearby cables, mains current, etc. In addition, analog cables generally have specific connector configurations that vary depending on the type of patient parameter being monitored. This can limit the number and/or combination of sensors that may be used with a particular patient monitoring device, since each port of the device is dedicated to a specific variety of sensor.

One or more of the foregoing problems, as well other problems, can be addressed, ameliorated, or resolved by certain embodiments of cables and related systems and methods described herein. In some embodiments, a system or cable that is configured to transmit information from a sensor to a patient monitoring device can include a circuit that provides the system or cable with a degree of intelligence. In some embodiments, the circuit stores information pertinent to operation of the cable, such as, for example, the type of physiological sensor with which the cable is configured to be coupled, the date of manufacture of the cable, the total time of active usage of the cable, etc. In other or further embodiments, the circuit can be configured to transition among two or more operational states, each of which can correspond to a different sensor configuration. For example, in some embodiments, the cable can be connected to a transducer that may be able to obtain different forms of invasive blood pressure readings, depending on the placement of a cannula within the patient's vasculature. A practitioner thus can select an appropriate setting for the circuit such that the operational state of the circuit corresponds with the particular variety of invasive blood pressure being monitored.

Other or further embodiments can include a circuit that is relatively close to the sensor and that converts analog signals to digital signals. The digital signals can then be transmitted through a length of cable to the monitoring devices. The digital signals can be less influenced by attenuation and/or less prone to distortion or other artifacts, as compared with analog signals. In other or further embodiments, cables that transmit the digital signals can have identical connectors for connecting with the monitoring devices, independent of the type of analog signal originally provided by the sensors. In certain of such embodiments, a variety of sensor combinations may be used with a given monitoring device. Additional embodiments are also disclosed herein.

Some embodiments are depicted in the drawings, wherein like elements may be designated by like numerals. In the following description, numerous specific details are provided for a thorough understanding of the embodiments described herein. However, those of skill in the art will recognize that one or more of the specific details may be omitted, or other methods, components, or materials may be used. Furthermore, the described features, operations, or characteristics may be combined in any suitable manner in one or more embodiments. It will also be readily understood that the order of the steps or actions of the methods described herein may be changed as would be apparent to those skilled in the art. Thus, any combination or order in the drawings or detailed description is for illustrative purposes only and is not necessarily meant to imply a required combination or order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

With reference to FIG. 1, in certain embodiments, a patient monitoring system 100 includes a patient monitor 110, a cable 112, a control unit 114, and a patient parameter sensor 116. The monitor 110 can include one or more connectors or ports 120 configured to communicate with the sensor 116. In some embodiments, the monitor 110 comprises one or more additional ports 122 that are configured to communicate with one or more additional sensors (such as, for example, other sensors described herein).

The monitor 110 can include one or more buttons or actuators 124 that are configured to effect one or more operations. In the illustrated embodiment, the actuators 124a, 124b, 124c, 124d, 124e comprise control buttons, which can, for example, be used to navigate through menus, make selections, or otherwise provide commands. The actuator 124f can comprise a power button.

The monitor 110 can include a display area 126 that is configured to display information in a visually perceivable format. For example, the display area 126 can include a screen 128 of any suitable variety, including those presently known and those yet to be devised. For example, the screen 128 can comprise a liquid crystal display (LCD) panel. In some embodiments, the screen 128 can be configured to receive information or otherwise interact with a medical practitioner. For example, the screen 128 can comprise a touch screen. In some embodiments, information received via one or more of the ports 120, 122 can be displayed on the screen 128.

The cable 112 can extend from a proximal end 130 to a distal end 132. In the illustrated embodiment, the cable 112 includes a connector 134 of any suitable variety at its proximal end 130. The connector 134 can be configured to be connected separately with any of the ports 120a, 120b, 120c, 120d. The cable 112 can include an electrical interface 136 at its distal end 132. In the illustrated embodiment, the electrical interface 136 comprises a connector 138 of any suitable variety. Extending between the connectors 134, 138 is a cable body 140. As discussed further below, the cable body 140 can include a plurality of electrical lines or electrical leads, which may be shielded and or otherwise encased.

The control unit 114 can be connected to the cable body 140. In the illustrated embodiment, the control unit 114 comprises a housing 142 configured to enclose or encase electrical components, and a portion of the cable body 140 extends into the housing 142 and is connected thereto. In other embodiments, the housing 142 is covered by or is integrally formed with a molding or an outer covering of the cable body 140. The illustrated embodiment of the control unit 114 further includes a plurality of control buttons or actuators 144, which are discussed further below.

The control unit 114 can include a cover 146 capable of rotating upward from the position shown in FIG. 1 so as to shield the actuators 144. The cover 146 can snap into place via a friction fit, or may be secured in the shielding position via any other suitable method. In further or other embodiments, the actuators 144 are recessed relative to a front face 148 of the housing 142 such that inadvertent contact with the actuators 144 may be reduced. In still further or other embodiments, actuation of a particular sequence or combination the actuators 144a, 144b, 144c, or a sustained actuation (e.g., depression) of one or more of the actuators 144a, 144b, 144c is required in order to effect a change of the control unit 114. Each of the mechanisms and methods discussed in this paragraph are examples of means for inhibiting accidental actuation of the actuators 144.

The control unit 114 can include a display 150 that is configured to provide visually perceivable information. Examples of information that may be displayed via the display 150 are discussed below. In some embodiments, the display 150 comprises a screen 152 of any suitable variety, including those presently known and those yet to be devised. For example, the screen 152 can comprise an LCD panel. In some embodiments, the screen 152 can be configured to receive information or otherwise interact with a medical practitioner. For example, in some embodiments, the screen 152 can comprise a touch screen, and in further embodiments, the functionality of one or more of the actuators 144 is provided by the touch screen.

In some embodiments, the control unit 114 is relatively small and can define a low profile. Although the illustrated embodiment of the control unit 114 is shaped substantially as a parallelepiped, other configurations are also possible. For example, the corners of the housing 142 can be smoothed or eliminated. In various embodiments, a maximum thickness of the housing 142 is within a range of from about 0.25 inches to about 1.0 inches, or is no more than about 1.0 inches, no more than about 0.5 inches, or no more than about 0.25 inches; a maximum width of the housing 142 is within a range of from about 1.0 inches to about 3.0 inches, or is no more than about 3.0 inches, no more than about 2.0 inches, or no more than about 1.0 inches; and a maximum height of the housing 142 is within a range of from about 0.5 inches to about 2.0 inches, or is no more than about 2.0 inches, no more than about 1.0 inches, or no more than about 0.6 inches. In various embodiments, a volume defined by the outer surface of the housing 142 is within a range of from about 2.0 cubic inches to about 5.0 cubic inches, or is no more than about 5.0 cubic inches, no more than about 3.0 cubic inches, or no more than about 2.0 cubic inches. In some embodiments, a viewable area of the screen 152 has a maximum width within a range of from about 0.5 inches to about 1.5 inches and a maximum height within a range of from about 0.25 inches to about 1.0 inches.

The control unit 114 can be closer to the distal end 132 of the cable 112 than it is to the proximal end 130. For example, in various embodiments, when the control unit 114 is electrically coupled with the sensor 116, the control unit 114 and the sensor 116 are within reach of each other such that the practitioner can position or adjust the sensor 116 and can manipulate the control unit 114 while the practitioner's feet remain in substantially the same position (e.g., without the practitioner walking between the sensor 116 to the control unit 114). In further embodiments, the control unit 114 can be positioned adjacent or near the sensor 116, or can be positioned adjacent or near the connector 138. In various further or other embodiments, the control unit 114 is at a distance of no greater than about 0.5 feet, no greater than about 1.0 feet, no greater than about 1.5 feet, no greater than about 2.0 feet, no greater than about 2.5 feet, no greater than about 3.0 feet, no greater than about 3.5 feet, or no greater than about 4.0 feet from one or more of the sensor 116, the distal end 132 of the cable 112, and the electrical interface 136 of the cable 112 (as measured along a length of the cable 112). In various embodiment, the control unit 114 is at a distance of no less than about 4.0 feet, no less than about 4.5 feet, no less than about 5.0 feet, no less than about 5.5 feet, no less than about 6.0 feet, or no less than about 6.5 feet from the proximal end 130 of the cable 112.

With continued reference to FIG. 1, the electrical interface 136 of the cable 112 can be configured to couple with the sensor 116. As used herein, the terms "couple" and "connect" can refer to one or more of a physical coupling or connection and an electrical coupling or connection. In some cases, the physical connection can be indirect. For example, in the illustrated embodiment, the sensor 116 comprises a pressure transducer 162, which is attached to a cable 164 that terminates in a connector 166. Coupling of the connectors 138, 166 can establish an electrical connection between the electrical interface 132 and the sensor 116, and further, can establish an indirect physical connection between the electrical interface 132 and the sensor 116, as the cable 164 physically separates the electrical interface 132 from the sensor 116. As discussed below, in other embodiments, the electrical interface 132 may be physically coupled directly to the sensor 116.

The pressure transducer 162 can interface with a pressurized fluid line 170. For example, in the illustrated embodiment, the pressure transducer 162 is mounted to a mounting plate 172 and is held in contact with the fluid line 170, which runs through or adjacent the mounting plate 170. Other suitable arrangements for the pressure transducer 162 are also possible. The source of pressurized fluid in the fluid line 170 can comprise, for example, a bag of saline solution 174 encompassed by a constricted sleeve 176.

The fluid line 170 can include a stopcock 178 in close proximity to the pressure transducer 162 that can be rotated so as to expose the fluid line 170 to atmospheric pressure (e.g., via a valve). When so positioned, the stopcock 178 can allow a baseline pressure of the fluid line 170 to be determined. For example, the pressure transducer 162 can be zeroed by actuating one or more of the actuators 144a, 144b, 144c of the control unit 114 when the fluid line 170 is exposed to atmospheric pressure, which can provide a reference pressure or baseline pressure against which fluctuations in the blood pressure of a patient 180 can be observed. Due to the proximity of the control unit 114 to the pressure transducer 162, in some embodiments, a practitioner can conveniently zero the pressure transducer 162 without a change in stance, such as, for example, without moving to a position within arm's length of one or more of the actuators 124a, 124b, 124c, 124d, 124e.

The fluid line 170 can be connected to a probing structure 190, such as, for example, a cannula 192 inserted in the vasculature of a patient. The cannula 192 can be of any suitable variety, and can be configured for insertion into the patient 180 in one or more specific positions. Those skilled in the art will recognize that a variety of placement options are available for the cannula 192, each of which can provide a different form of invasive blood pressure measurement. For example, the cannula 192 can be configured for insertion into the patient 180 so as to monitor the arterial blood pressure, central venous pressure, pulmonary artery pressure, or intracranial pressure of the patient 180. Each separate placement of the cannula 192 can represent a different configuration of the sensor 116.

Figure 2:
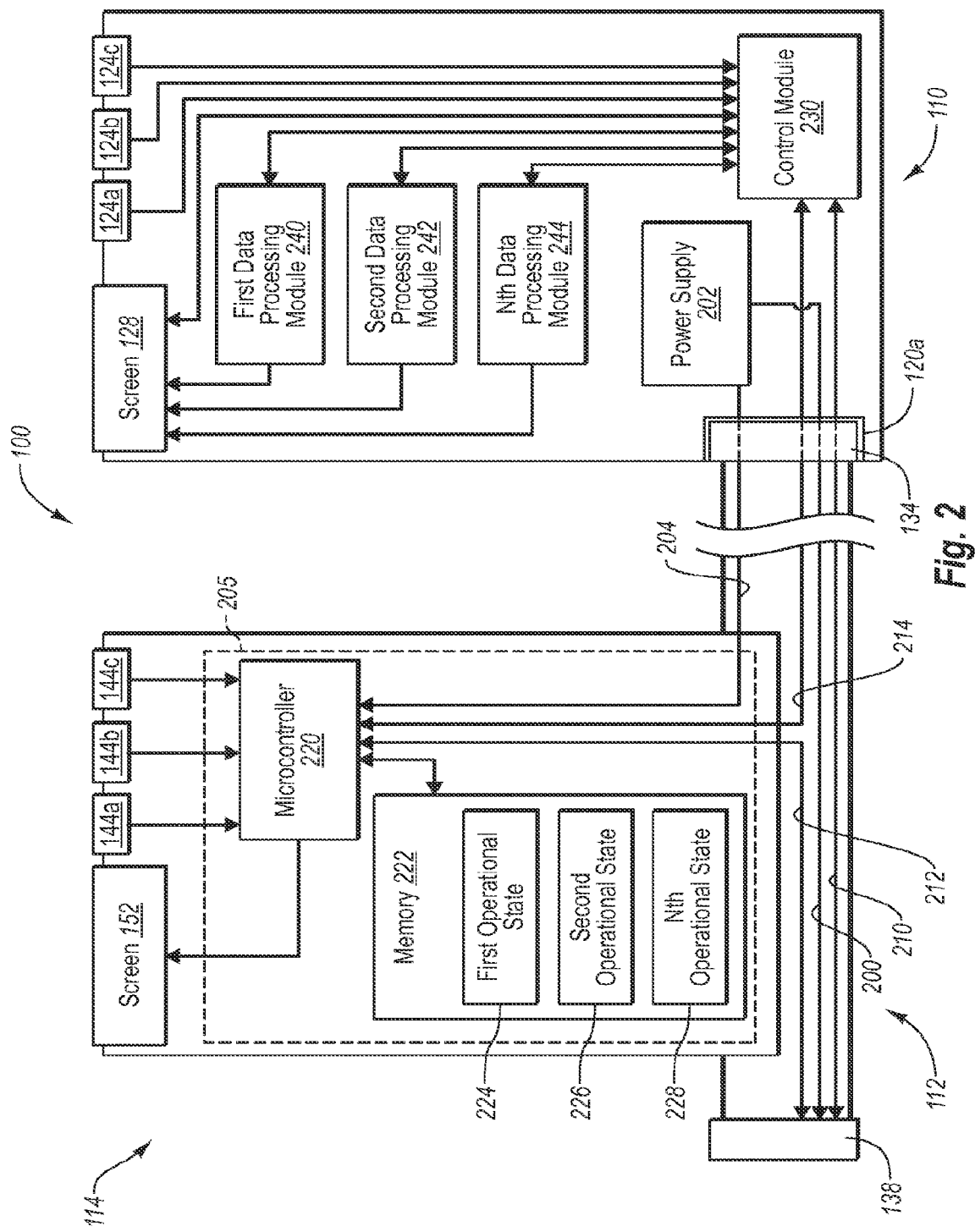
FIG. 2 is a simplified block diagram schematically illustrating the monitor and the cable of FIG. 1 in a coupled state.

FIG. 2 is a simplified block diagram schematically illustrating the monitor 110, the cable 112, and the control unit 114 of the system 100. The proximal connector 134 is shown coupled with the port 120a, and the distal connector 138 is shown in an uncoupled state. In certain embodiments, one or more power leads 200 extend between the proximal and distal connectors 134, 138. In some embodiments, the one or more power leads 200 can be configured to provide electrical power to the sensor 116 from a power supply 202 of the monitor 110. In other embodiments, the sensor 116 is configured to operate without power from the monitor 110, and the cable 112 may not include the one or more power leads 200.

The cable 112 can include one or more power leads 204 configured to couple an electrical circuit 205 of the control unit 114 with the power supply 202 of the monitor 110. The one or more power leads 204 can extend between the proximal connector 134 and the circuit 205.

One or more communication leads 210 can extend between the proximal and distal connectors 134, 138. The one or more communication leads 210 can be configured to transmit information between the sensor 116 and the monitor 110. In some embodiments, the cable 112 includes one or more communication leads 212 extending between the distal connector 138 and the circuit 205. Accordingly, in some embodiments, the circuit 205 can communicate directly with the sensor 116. In other embodiments, the circuit 205 communicates with the sensor 116 only indirectly (e.g., via the monitor 110), and thus may not include the communication lead 212.

The cable 112 can include one or more communication leads 214 extending between the proximal connector 134 and the circuit 205. As further discussed below, the circuit 205 can be configured to communicate with the monitor 110 via the communication lead 214 when the proximal connector 134 is connected to the monitor 110.

The circuit 205 can comprise a microcontroller 220 and/or other microelectronic components. The microcontroller 220 can be configured to receive input from the actuators 144a, 144b, 144c, the monitor 110 (via the one or more communication leads 214), and/or a memory device or memory 222. The microcontroller 220 can be configured to output information to the screen 152, and can be configured to store information in the memory 222 and/or access information stored in the memory 222. Although the microcontroller 220 and the memory 222 are shown as separate components in the schematic diagram shown in FIG. 2, in some embodiments, the memory 222 can be integral with the microcontroller 220.

The memory 222 can be configured to store a variety of information regarding the cable 112, and the information can be updated or otherwise altered via the microcontroller 220. In some embodiments, the information stored in the memory 222 comprises information regarding the cable 112 itself, such as its manufacturer, date of manufacture, date of first operation, most recent period of active usage, cumulative total time of active usage, expiration date, settings from previous uses, and/or other information. In further or other embodiments, the memory 222 can store information related to or unrelated to the operation of the cable 112, such as the scale settings for a patient parameter that may be or is being monitored (e.g., pressure, temperature, or voltage), alarm limits for a particular monitoring event, information regarding the patient 180 being monitored, information regarding the pressurized saline bag 174, etc. Additionally, in some embodiments, information can be erased from the memory 222. For example, information regarding the identity of a patient can be erased upon discharge of the patient. In some embodiments, a user may select a preferred language in which to display stored information (or other information) via the screen 152.

In some embodiments, the memory 222 can store information regarding different operational states of the circuit 220, which correspond with different operational states of the cable 112. For example, as previously discussed, a given sensor 116 (or different sensors 116) can operate in a variety of different sensor configurations, depending on the placement of a probing structure 190 relative to a patient 180. Thus, for example, the transducer 162, and hence the cable 112 when it is coupled to the transducer, can be configured to operate in any of an arterial blood pressure sensing configuration, a central venous pressure sensing configuration, a pulmonary arterial pressure sensing configuration, an intracranial pressure sensing configuration, or other pressure sensing configuration. Particular information regarding each possible configuration in which a sensor 116 (and cable 112) may operate can be stored in the memory 222. For example, information can be stored regarding one or more of a first operational state 224, a second operational state 226, and any additional operational state up to and including an Nth operational state (where "N" represents any suitable integer). Each operational state stored in the memory 222 can also be referred to as a channel.

Information regarding an operational state 224, 226, 228 can include a label or text that is representative of that state (e.g., "ART" for arterial pressure or "ICP" for intracranial pressure), which can be displayed via the screen 152 when the operational state has been selected. The information likewise can include instructions that can be delivered to the monitor 110 via the communication lead 214 upon selection of an operational state.

An operational state 224, 226, 228 can be selected via actuation of one or more of the actuators 144a, 144b, 144c. Likewise, the actuation of one or more of the actuators 144a, 144b, 144c can be used to transition among the operational states 224, 226, 228. Reference herein to actuating one or more of the actuators 144a, 144b, 144c can indicate that one of the actuators may be actuated, two of the actuators may be actuated in combination (e.g., in series, in tandem, etc.), or any other suitable actuation combination is possible to achieve the stated action. In various embodiments, one or more of the actuators 144a, 144b, 144c can be actuated to transition the circuit 205 among two or more, three or more, four or more, or any other suitable number of operational states. Selection of an operational state 224, 226, 228 can result in the circuit 205 operating in the selected operational state. For example, upon the selection of an operational state, the microcontroller 220 can deliver instructions regarding the operational state to a control module 230 of the monitor 110.

In other or further embodiments, one or more of the actuators 144a, 144b, 144c can be actuated to effect a change in the circuit 205 other than to transition among the operational states 224, 226, 228. For example, as discussed above one or more of the actuators 144a, 144b, 144c can be actuated to "zero" or otherwise calibrate a patient parameter sensor 116 (e.g., the transducer 162). Another example includes instigating a diagnostic check of the cable, such as to ensure that none of the leads 200, 204, 210, 212, 214 contain any discontinuities. Yet another example includes actuating one or more of the actuators 144a, 144b, 144c to access, alter, or erase information stored in the memory 222, or to store information in the memory 222.

In some embodiments, the monitor 110 is configured to process information received via the port 120a in a mode that corresponds with an operational state of the cable 112 and the circuit 205. In the illustrated embodiment, the monitor 110 comprises a first data processing module 240, a second data processing module 242, and additional data processing modules up to and including an Nth data processing module 244 (where "N" represents any suitable integer). When the monitor 110 processes information received by the port 120a via one of the data processing modules 240, 242, 244, the monitor 110 can be referred to as operating in an operational mode associated with that data processing module 240, 242, 244. Stated otherwise, each data processing module 240, 242, 244 can define a separate channel of the monitor 110, and the channels of the monitor can correspond with the channels of the circuit 205. In various embodiments, the monitor 110 can be configured to operate in one or more, two or more, three or more, four or more, or any other suitable number of operational modes or channels.

Each data processing module 240, 242, 244 can include an algorithm or other data processing system suitable for a particular sensor configuration. Thus, for example, the first data processing module 240 may be particularly suited to process information regarding arterial pressure, whereas the second data processing module 242 may be particularly suited to process information regarding intracranial pressure. The control module 230 is configured to receive instructions regarding a selected operational state of the circuit 205 and, based on this information, to automatically route information received via the one or more communication leads 210 to the appropriate or associated data processing module 240, 242, 244. The processed information can be displayed via the screen 128.

With continued reference to FIG. 2, the ports 120a, 120b, 120c, 120d can be substantially interchangeable. For example, in some embodiments, the schematic diagram of the monitor 110 would be substantially the same if the port 120a were replaced with any of the ports 120b, 120c, 120d (see FIG. 1). Accordingly, if the cable 112 were disconnected from the port 120a (e.g., from the configuration shown in FIG. 2) and connected with any of the ports 120b, 120c, 120d, the monitor 110 would automatically select a data processing module 240, 242, 244 corresponding with the operational state of the circuit 205. The monitor 110 thus can automatically conform to or synchronize with one or more cables 112 connected thereto, and can automatically process information received via the ports 120a, 120b, 120c, 120d in one or more operational modes that correspond with the operational states of the one or more cables 112 (or their associated circuits 205) respectively. In some embodiments, selection of a data processing module 240 occurs substantially simultaneously with connection of a cable 112 to the monitor 110.

In certain embodiments, the monitor 110 can access information stored in the memory 222 via the control module 230, and can display the same via the screen 128. Likewise, in some embodiments, the actuators 124 can be used to access, alter, delete, or store information in the memory 222.

FIG. 3 illustrates another embodiment of a monitor 310 connected with another embodiment of a cable 312 that includes an embodiment of a control unit 314. The monitor 310, the cable 312, and the control unit 314 can resemble the monitor 110, the cable 312, and the control unit 114, respectively, thus like features are represented by like reference numerals, with the leading digit incremented to "3." The control unit 314 can include a circuit 305 that includes a wireless communicator 395. The monitor 310 can include a wireless communicator 396 configured to communicate with the wireless communicator 395. Comparison of FIGS. 2 and 3 illustrates that the wireless communicators 395, 396 can replace the communication lead 214. Any suitable variety of wireless communicators 395, 396 are possible, including RFID systems, Bluetooth systems, infrared systems, etc.

Figure 4:
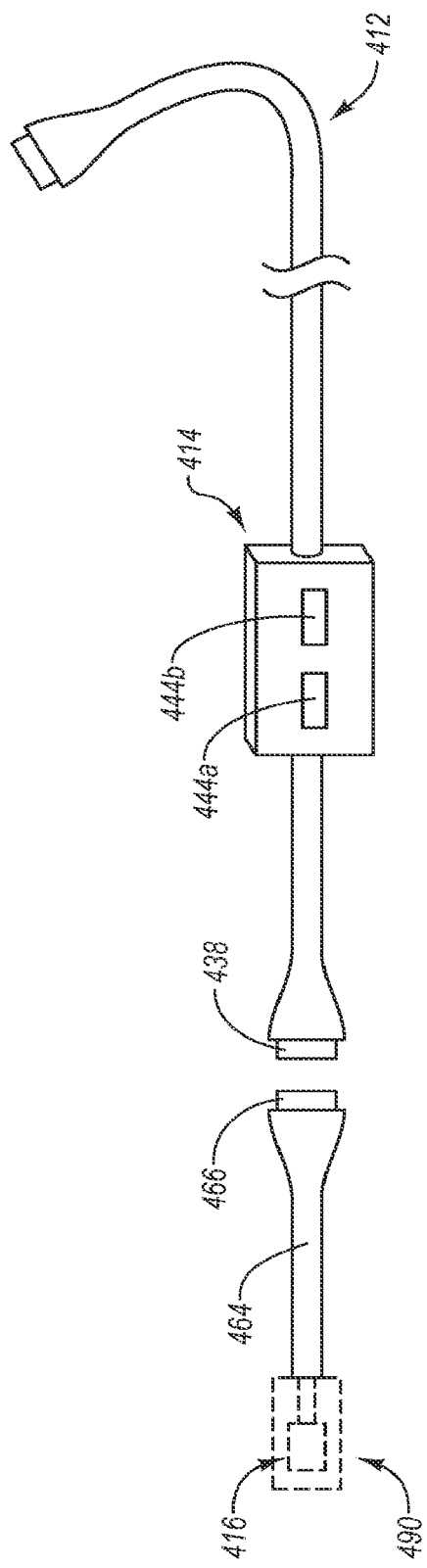
FIG. 4 is a perspective view of another embodiment of a cable that includes another embodiment of a control unit and an embodiment of a patient parameter sensor with which the cable is configured to couple.

FIG. 4 illustrates another embodiment of a cable 412 that includes an embodiment of a control unit 414. The cable 412 can be selectively connected with a cable 464, which can include a proximal connector 466, a probing structure 490, and a sensor 416. The cable 412 and components thereof can resemble the cables 112, 312 and components thereof, and the cable 464 and components thereof can resemble the cable 164 and components thereof, thus like features are represented by like reference numerals, with the leading digit incremented to "4."

The illustrated control unit 414 includes two actuators 444a, 444b. As with the actuators 144 of the control unit 114, more or fewer actuators 444 are possible, and may vary depending on the desired functionality of the control unit 414. In the illustrated embodiment, the actuator 444a is configured to select a channel or operational state of the cable 412, and the actuator 444b is configured to zero the sensor 416 and/or instigate a sensing event via the sensor 416.

The control unit 414 also differs from the embodiment of the control unit 114 illustrated in the FIGS. 1 and 2 in that it does not include a display. In some embodiments, the control unit 414 is configured to communicate with a monitor (such as the monitors 110, 310 discussed above) such that a screen of the monitor can be used to display information supplied by the control unit 414. Thus, for example, a channel selected via the actuator 444a can be displayed on a screen of the monitor, rather than on the control unit 414 itself.

In the illustrated embodiment, the sensor 416 is integral with the probing structure 490. For example, in some embodiments the sensor 416 and the probing structure 490 comprise a temperature probe (e.g., a probe that includes a thermistor). Other types and arrangements are possible for the sensor 416 and the probing structure 490. For example, in some embodiments, a cuff system for measuring noninvasive blood pressure can comprise the probing structure 490 and the sensor 416. Other arrangements of the probing structure 490 and the sensor 416 can be suitable for measuring patient parameters such as, for example, respiration activity, cardiac activity, brain activity, etc.

Figure 5:
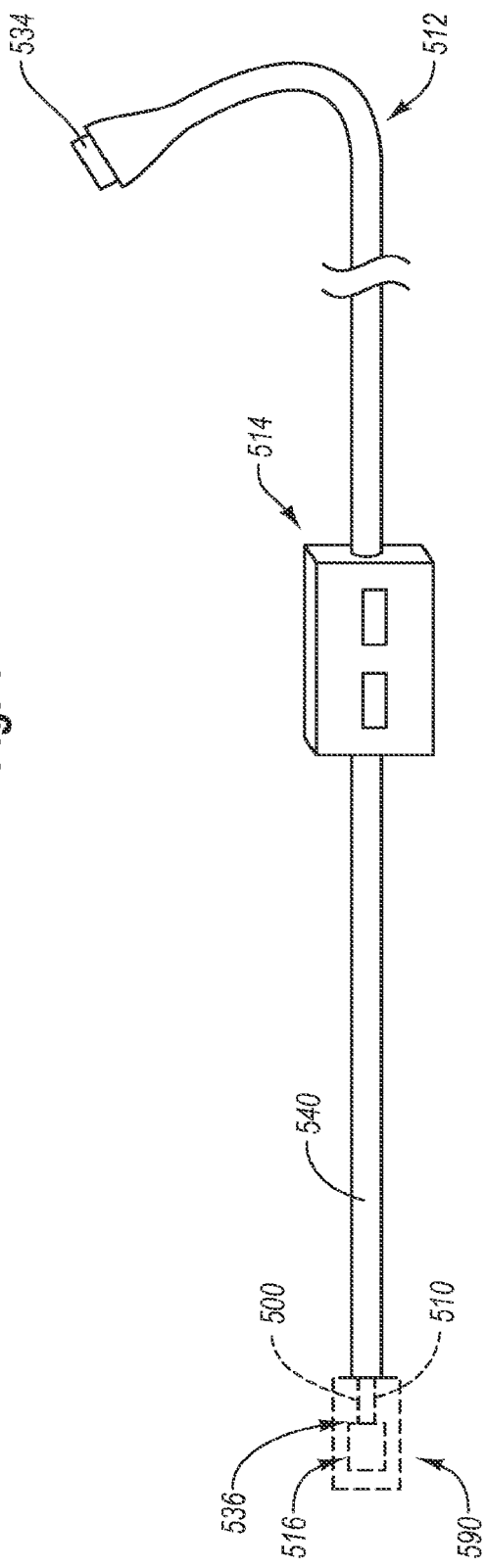
FIG. 5 is a perspective view of another embodiment of a cable that includes another embodiment of a control unit and is integrally connected with an embodiment of a patient parameter sensor.

FIG. 5 illustrates another embodiment of a cable 512 that includes an embodiment of a control unit 514. The cable 512 and components thereof can resemble the cables 112, 312, 412 and components thereof, thus like features are represented by like reference numerals, with the leading digit incremented to "5." In the illustrated embodiment, the cable 512 includes a cable body 540 coupled with the probing structure 590 in a direct physical engagement. The cable body 540 can include a power lead 500 and a communication lead 510, each of which can be coupled with a connector 534 at a proximal end thereof and coupled with a sensor 516 at a distal end thereof. An electrical interface 536 of the cable 512 thus can include the distal ends of the power lead 500 and the communication lead 510.

Figure 6:
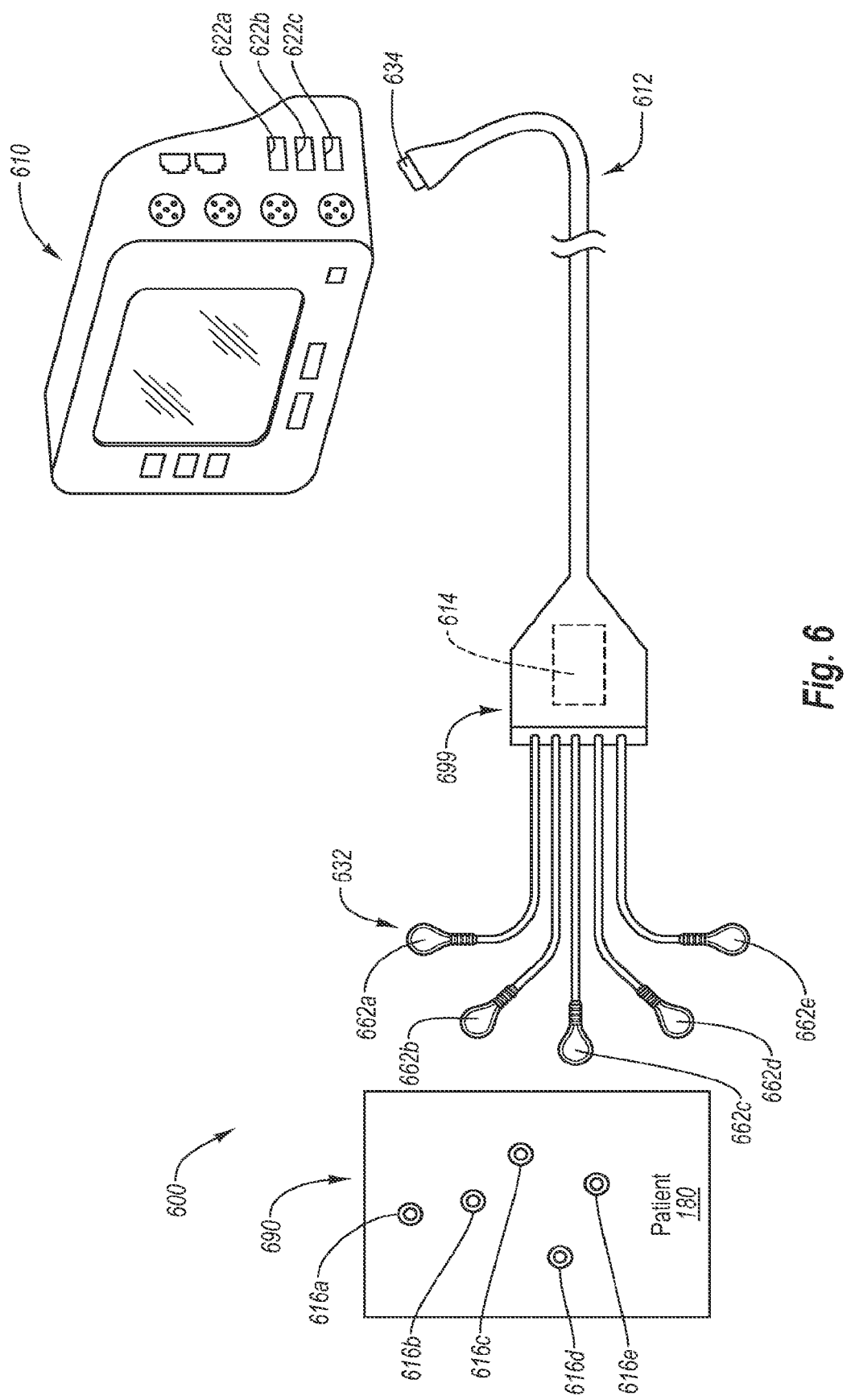
FIG. 6 is a partially exploded perspective view of another embodiment of a patient monitoring system including another embodiment of a monitor, cable, and control unit.

FIG. 6 illustrates another embodiment of a patient monitoring system 600 such as the patient monitoring system 100 discussed above. Like features are represented by like numerals, with the leading digit incremented to "6." The system 600 can include a monitor 610 and a cable 612. Embodiments of the monitor 610 can include features of one or more of the monitors 110, 310 discussed above. The monitor 610 can include one or more ports 622a, 622b, 622c.

The cable 612 can be particularly suited for use in electrocardiography, and can comprise multiple leads 662 that extend from a yoke 699. As one skilled in the art will appreciate, the cable 612 can comprise more of fewer leads 662 than those shown in FIG. 6. The distal ends of the leads 662 can define an electrical interface 632 of the cable 612. The electrical interface 632 can be configured to couple with a probing structure 690, which can comprise a plurality of sensors 616 (e.g., electrodes) that can be coupled to the patient 180.

The cable 612 can comprise a control unit 614 such as any of the control units 114, 314, 414, 514 discussed above. In particular, features of any of the previously discussed control units can be incorporated into the control unit 614, and vice versa. In the illustrated embodiment, the control unit 614 is completely embedded within the cable 612. In some embodiments, the control unit 614 does not include a screen, and in further embodiments, does not include any actuators.

Figure 7:
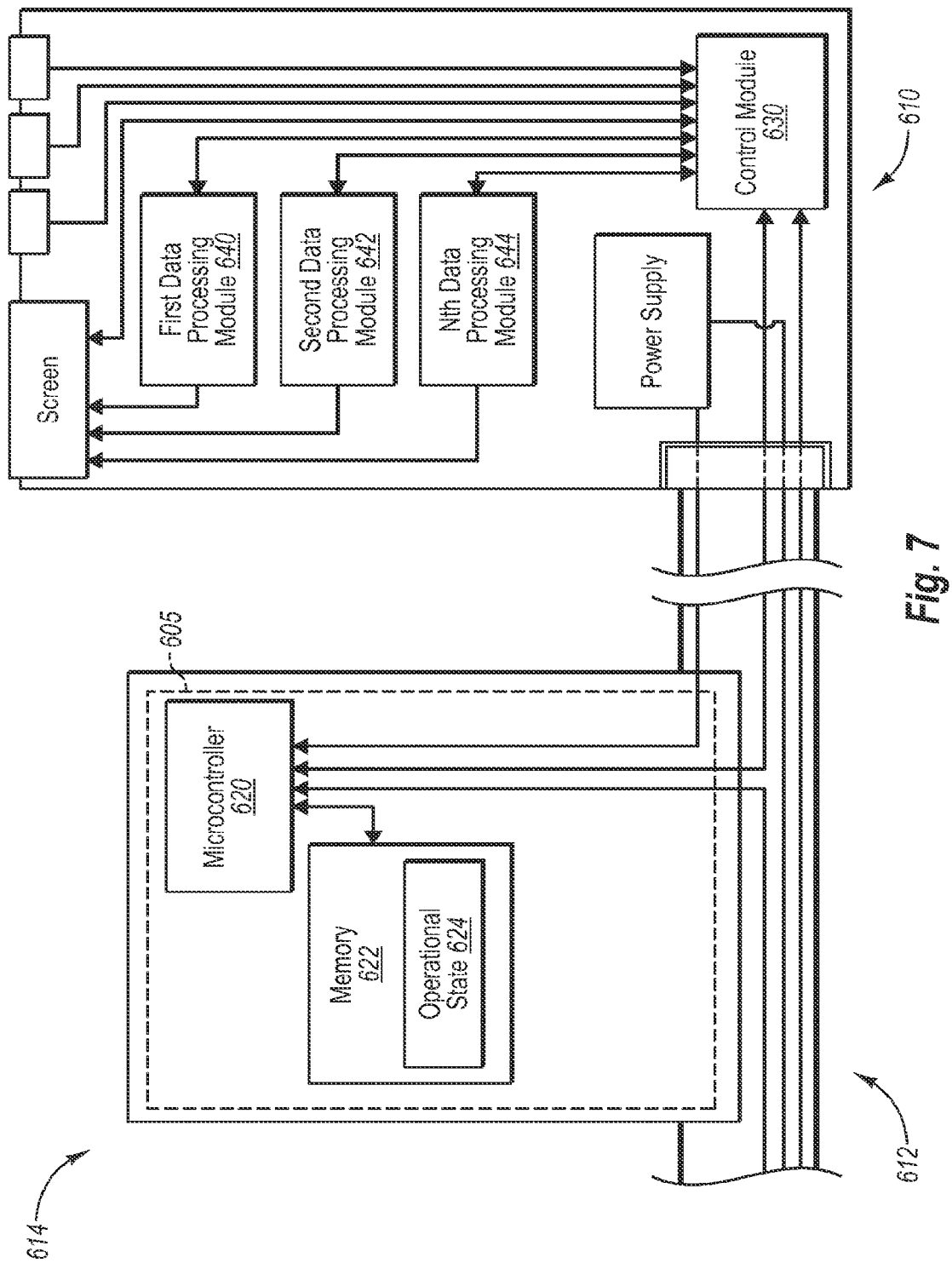
FIG. 7 is a simplified block diagram schematically illustrating the monitor and the cable of FIG. 6 in a coupled state.

FIG. 7 is a simplified block diagram schematically illustrating the monitor 610, the cable 612, and the control unit 614 of FIG. 6. Like the monitors 110, 310, the monitor 610 can have one or more data processing modules. In the illustrated embodiment, the monitor 610 includes a first data processing module 640, a second data processing module 642, and an Nth data processing module 644. Each data processing module 640, 642, 644 can be configured to operate with a corresponding operational state of a cable. The monitor 610 can also include a control module 630 such as the control module 230.

The control unit 614 can include a circuit 605, which may include one or more of a microcontroller 620 and a memory device 622. In some embodiments, a microcontroller is not used.

In the illustrated embodiment, the cable 612 includes a single operational state 624, which may be stored in the memory device 622. The operational state 624 can include stored instructions regarding operation of the cable 612, as well as any other suitable information (such as that discussed above with respect to the cable 112). Additionally, the stored instructions can include, for example, information regarding the number of leads 662 possessed by the cable 612.

Upon coupling the cable 612 with the monitor 610, the control module 630 can access information regarding the operational state 624, and can automatically transition the monitor 610 into an operational mode that employs the first data processing module 640 to process information received via the leads 662 of the cable 612. Stated otherwise, based on the information received from the circuit 605, the monitor 610 can automatically select an appropriate channel for processing information obtained via the cable 612.

As previously mentioned, features described with respect to of any of the cables 112, 312, 412, 512, and 612 can be combined in any suitable arrangement. The same is true of other similarly numbered components or features, such as the control units 114, 314, 414, 514 and the monitors 110, 310, 610. Additionally, sub-combinations of the disclosed features are also contemplated, and may represent additional embodiments.

For example, with reference again to FIGS. 1 and 2, in certain embodiments, the cable 112 does not communicate information regarding its operational state to the monitor 110 when the connector 134 is coupled with the port 120a. For example, in some embodiments, the cable 112 does not include the communication lead 204. The control unit 114 can otherwise be substantially the same as that depicted in FIG. 2, and can include one or more of the operational states 224, 226, 228. Transition among the operational states 224, 226, 228 can be effected by actuation of one or more of the actuators 144a, 144b, 144c. Each of the operational states 224, 226, 228 can include information, such as textual information or other data, regarding a specific sensor configuration with which the cable 112 is configured to operate. For example, one operational state 224 can include instructions for displaying the text "ART" via the screen 152 to represent that the cable 112 is being used to monitor arterial blood pressure, whereas another operational state 226 can include instructions for displaying the text "ICP" via the screen 152 to represent that the cable 112 is being used to monitor intracranial pressure. However, the operational states 224, 226, 228 may be devoid of instructions for switching the monitor 110 among its various operational modes. The operational modes can instead be selected via one or more of the actuators 124*a*, 124*b*, 124*c* of the monitor 110 (e.g., the actuators 124*a*, 124*b*, 124*c* can be used to cycle through the data processing modules 240, 242, 244).

In further or other embodiments, information other than information regarding the operational state of the cable 112 can be stored in the memory 222 and/or displayed via the screen 152. Non-limiting examples of such other information that can be stored and/or displayed are provided elsewhere in this disclosure.

As another example, in certain embodiments, the cable 112 includes the communication lead 204, but the control unit 114 is devoid of actuators 144*a*, 144*b*, 144*c*. In some embodiments, the control unit 114 can function substantially as a follower or echo device relative to the monitor 110. For example, an operational mode of the monitor 110 can be selected via one or more of the actuators 124*a*, 124*b*, 124*c* (e.g., a data processing module 240, 242, 244 can be selected). The control unit 114 can be configured to receive information from the monitor 110 regarding the selected operational mode, and can automatically select a corresponding operational state 224, 226, 228. In other or further embodiments, information displayed via the screen 150 of the control unit 114 can be selectively controlled via interaction with the monitor 110, such as by actuating one or more of the actuators 124*a*, 124*b*, 124*c*.

Figure 8:
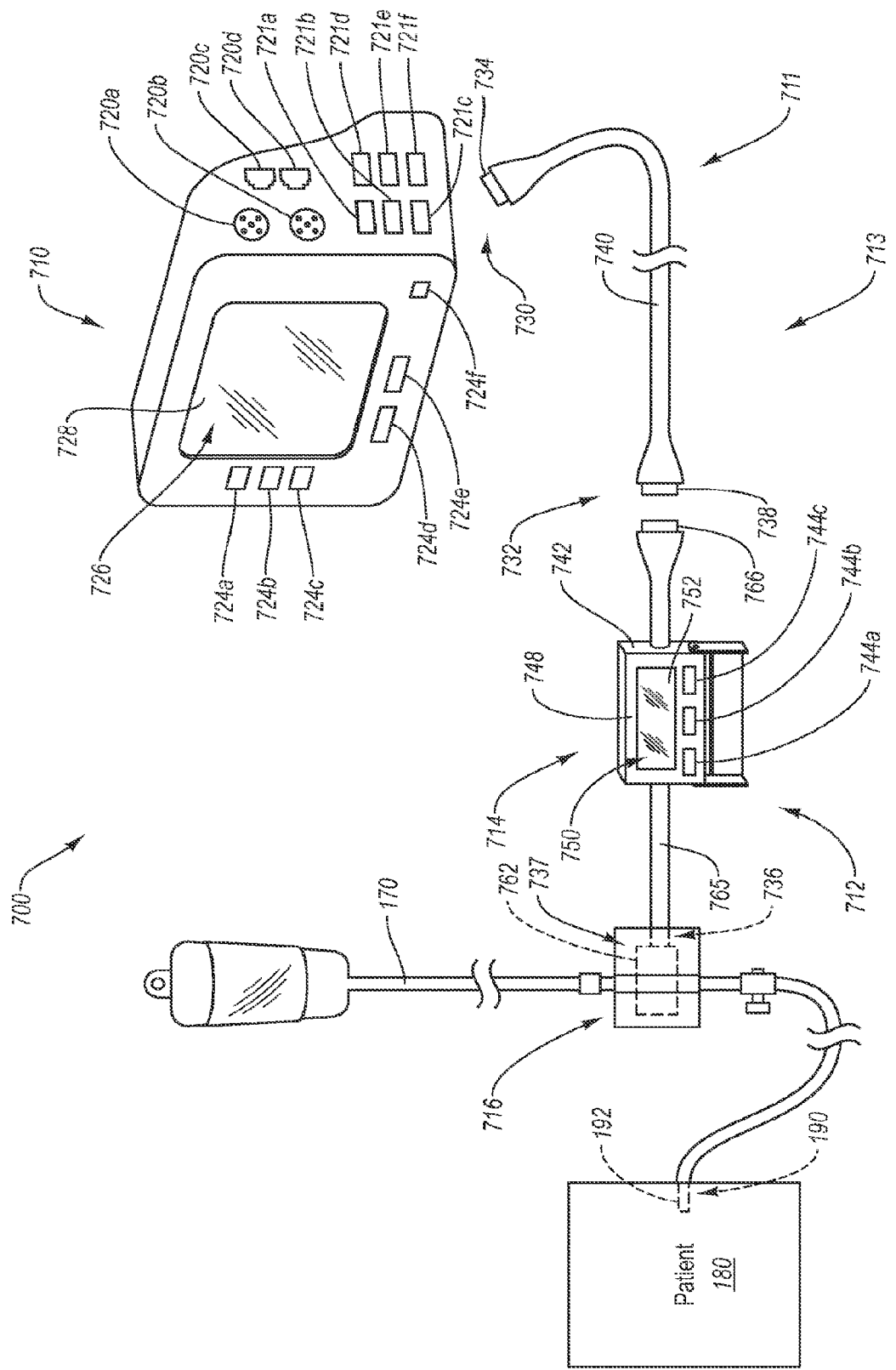
FIG. 8 is partially exploded perspective view of another embodiment of a patient monitoring system.

FIG. 8 illustrates another embodiment of a patient monitoring system 700. The system 700 can resemble the systems 100, 600. Features of the system 700 resembling those of the system 100 may be represented by like numerals, with the leading hundreds digit incremented from "1" to "7" or from "2" to "8". Accordingly, the applicable portions of the disclosure regarding the systems 100, 600, and components thereof, apply equally to the similarly numbered features of the system 700, and components thereof. Likewise, applicable portions of the following disclosure apply to the systems 100, 600, and to components thereof.

The system 700 can include a patient monitor 710, which can include features of one or more of the monitors 110, 310, 610 discussed above. For example, the monitor 710 can include a display area 726, a screen 728, and/or one or more actuators 724*a*, 724*b*, 724*c*, 724*d*, 724*f*. In some embodiments, the monitor 710 comprises one or more analog ports 720*a*, 720*b*, 720*c*, 720*d*. The ports 720*a*, 720*b*, 720*c*, 720*d* may have different shapes and/or different numbers of electrical contacts, depending on the type of sensors with which they are configured to be coupled. In some embodiments, one or more of the ports 720*a*, 720*b*, 720*c*, 720*d* can resemble the ports 120 described above, and may be configured to couple with cables such as the cables 112, 312, 412, 512, 612 in the manners described above. In other or further embodiments, the monitor 710 includes one or more digital ports 721*a*, 721*b*, 721*c*, 721*d*, 721*e*, 721*f*. In certain embodiments, each of two or more of the digital ports 721*a*, 721*b*, 721*c*, 721*d*, 721*f* are identical to each other such that a given connector can be selectively or interchangeably coupled therewith.

The patient monitoring system 700 can include an information delivery system 713, which can include one or more cables. In the illustrated embodiment, a proximal cable 711 extends from a proximal end 730 to a distal end 732. The cable 711 includes a proximal connector 734 that is configured to be connected separately with any of the ports 721*a*, 721*b*, 721*c*, 721*d*, 721*e*, 721*f*. The cable 711 further includes a cable body 740 that extends from the proximal connector 734 to a distal connector 738, which is situated at the distal end 732 of the cable 711. In various embodiments, a length of the cable body is no less than about 2.0 feet, no less than about 3.0 feet, no less than about 4.0 feet, no less than about 5.0 feet, no less than about 6.0 feet, or no less than about 7.0 feet.

A distal cable 712 can include a proximal connector 764 that is configured to couple with the distal connector 738 of the cable 711. The cable 712 can include an electrical interface 736 that is electrically coupled with a sensor 716. The electrical interface 736 can be at a distal end 737 of the cable 712. In the illustrated embodiment, the electrical interface 736 comprises one or more lead lines and/or power lines, and is directly physically coupled with the sensor 716 (thus resembling the electrical interface 536). In other embodiments, the electrical interface 736 includes one or more connectors via which the cable 712 is indirectly physically coupled with the sensor 716 (thus resembling the electrical interface 136).

The electrical interface 736 can receive analog signals from the sensor 716. In particular, the sensor can be configured to convert measured quantities of physical properties, such as, for example, pressure (e.g., blood pressure) or voltage (e.g., electrical activity of the heart), into electrical signals that are representative of the quantities measured. For example, in some embodiments, the sensor 716 is configured to generate electrical waveforms that are representative of fluctuations of a patient parameter, and these waveforms can be transmitted via the electrical interface 736.

The distal cable 712 can include a cable body 765, which can extend between the connector 766 and the electrical interface 736. In some embodiments, a control unit 714 is coupled with the cable body 765 in any suitable manner, such as those described with respect to the control unit 114 and the cable body 140. For example, in some embodiments, the control unit 714 is integrated into the cable body 765. The control unit 714 can resemble any of the control units 114, 314, 414, 514, 614 described above. In various embodiments, the control unit 714 can include a housing 742, a display 750, a screen 752, and/or one or more actuators 744*a*, 744*b*, 744*c*. The control unit 714 can be configured to operate in substantially the same manner as any of the control units 114, 314, 414, 514, 614. However, as further discussed below, in some embodiments, the control unit 714 can include one or more additional and/or different functionalities, such as the conversion of analog signals received from the sensor 116 into digital signals.

The control unit 714 can be positioned relatively close to the sensor 716 so as to reduce, minimize, or even eliminate the length of the cable body 765 through which analog signals from the sensor 716 pass to reach the control unit 714. For example, in some embodiments, the control unit 714 is integral with the sensor 716 and/or is adjacent thereto. In various other embodiments, the length of the cable body 765 through which analog signals pass to the control unit 714 is no more than about 0.5 feet, no more than about 1.0 feet, no more than about 2.0 feet, or no more than about 3.0 feet.

The control unit 714 likewise can be positioned relatively close to the connector 766. For example, in some embodiments, the connector 766 is integral with the control unit 714 such that the portion of the cable body 714 between the connector 766 and the control unit 714 is omitted. In other embodiments, the length of the cable body 765 between the control unit 714 and the connector 766 is no more than about 0.5 feet, no more than about 1.0 feet, no more than about 2.0 feet, or no more than about 3.0 feet.

In some embodiments, the cable 711 may be omitted from the information delivery system 713, and the cable 712 may be lengthened. Accordingly, in some embodiments, the connector 766 is configured to be coupled with any of the ports 721*a*, 721*b*, 721*c*, 721*d*, 721*e*, 721*f*. The portion of the cable 712 that is proximal of the control unit 714 can define any of the lengths described above with respect to the cable 711. For example, in various embodiments, a length of the cable body 765 between the control unit 714 and the connector 766 is no less than about 2.0 feet, no less than about 3.0 feet, no less than about 4.0 feet, no less than about 5.0 feet, no less than about 6.0 feet, or no less than about 7.0 feet.

Any of the lengths recited relative to the cables 711, 712 can correspond to distances between portions of the system 713 when the system 713 is in an assembled state and the cables 711, 712 are fully extended (e.g., are stretched out so as to be substantially linear). For example, in some embodiments, when the connector 734 is coupled with a port 721 and the connectors 738 and 766 are coupled to each other, the cable bodies 740, 765 can be straightened, and a distance between the control unit 714 and the patient monitor 710 can be no less than about 2.0 feet, no less than about 3.0 feet, no less than about 4.0 feet, no less than about 5.0 feet, no less than about 6.0 feet, or no less than about 7.0 feet.

The sensor 716 can comprise any suitable sensor device, such as those described above. In the illustrated embodiment, the sensor 762 comprises a pressure transducer 762 coupled with the pressurized fluid line 170. The fluid line 170 can terminate at the probing structure 190, which comprises the cannula 192 in the illustrated embodiment. As discussed above, placement of the cannula 192 in different portions of the vasculature of the patient 180 can permit monitoring of different varieties of invasive blood pressure. The different placements of the cannula 192 thus can represent different sensor configurations.

Figure 9:
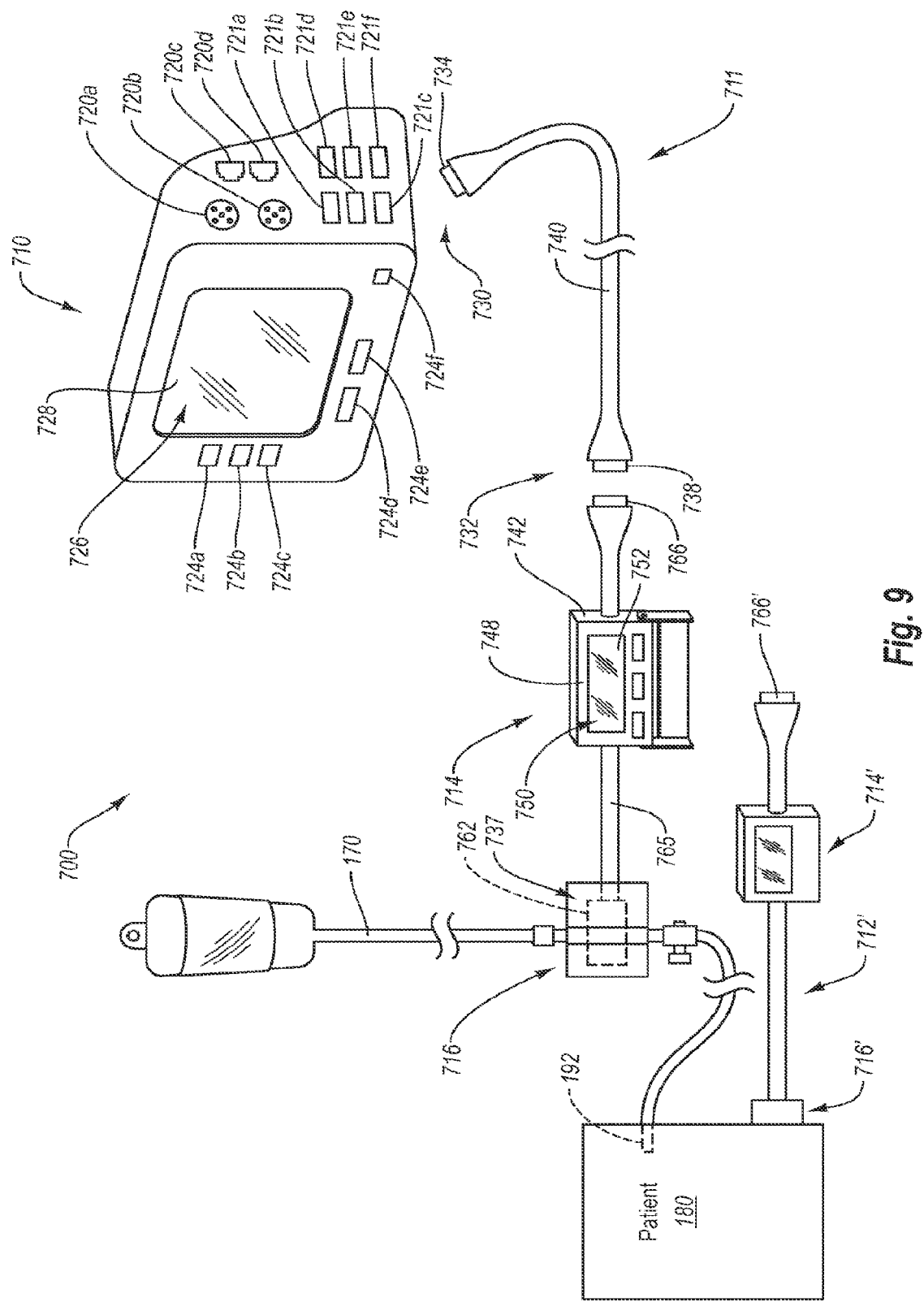
FIG. 9 is a partially exploded perspective view of another embodiment of a patient monitoring system.

As shown in FIG. 9, in some embodiments, the patient monitoring system 700 can include a plurality of cables 712, 712', control units 714, 714', and/or patient parameter sensors 716, 716'. In the illustrated embodiment, the sensor 716' is configured to gather information regarding a patient parameter that is different from the patient parameter tracked by the sensor 716. For example, in some embodiments, the sensor 716' can be configured to generate analog electrical signals bearing blood pressure information obtained noninvasively, whereas the sensor 716 is configured to generate analog electrical signals bearing blood pressure information obtained invasively. The sensors 716, 716' can be configured to obtain information regarding any other suitable types and combinations of patient parameters, such as, for example, respiration activity, cardiac activity, volume changes (e.g., for plethysmography), etc. Accordingly, in some embodiments, each control unit 714, 714' may operate in a different state.

Each of the control units 714, 714' can be configured to convert analog signals into digital signals. In certain embodiments, the cable 711 can be used with either of the control units 714, 714'. For example, the connector 738 can be configured to connect with either connector 766, 766'. Moreover, the connector 734 can be configured to connect with any of the ports 721*a*, 721*b*, 721*c*, 721*d*, 721*e*, 721*f*. In further embodiments, separate cables 711 can be used interchangeably with each of the control units 714, 714', and each of the control units 714, 714' may be simultaneously in connection with the monitor.

Figure 10:
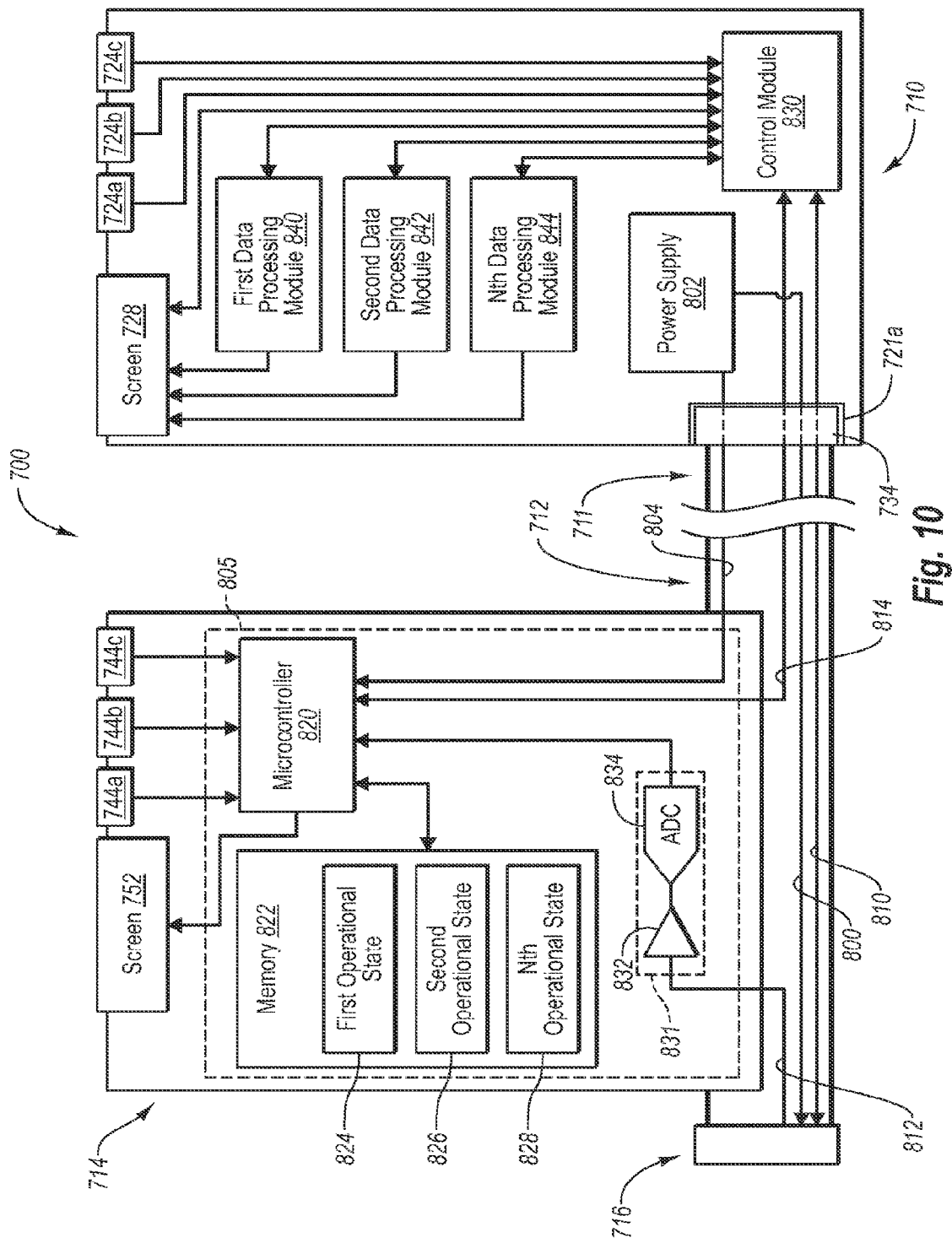
FIG. 10 is a simplified block diagram schematically illustrating a monitor and a control unit of the system of FIG. 9 in a coupled state.

FIG. 10 is a simplified block diagram schematically illustrating the monitor 710, the cables 711, 712, and the control unit 714 of the system 700. The proximal connector 734 is shown coupled with the port 721*a*, and the sensor 716 is shown in an uncoupled state (i.e., disconnected from the pressurized fluid line 170). The connectors 738, 766 (see FIGS. 8 and 9) are coupled to each other, but are not shown.

The cables 711, 712 can include one or more power leads 800, 804 and communication leads 810, 814. Additionally, the cable 712 can include a communication lead 812. The patient monitor 710 can include a power supply 802 and a control module 830, and can further include one or more data processing modules 840, 842, 844. The control unit 714 can include a circuit 805, which can include a microcontroller 820 and/or a memory 822. The memory 822 can store information regarding one or more operational states 824, 826, 828 of the circuit 805. The foregoing components and features can function similarly to the analogously numbered components and features of the system 700. For example, if the circuit 805 is in the first operational state 824, the control module 830 can automatically deliver digital information received from the control unit 714 to the first data processing module 840. As a further example, if the circuit 805 is changed to the second operational state 826, such as via actuation of one or more of the actuators 744*a*, 744*b*, 744*c*, the control module 830 can automatically deliver digital information received from the control unit 714 to the second data processing module 842. As a further example, if the circuit 805 is changed to the Nth operational state 828, and the connector 734 is coupled with a different port, such as any of the ports 721*b*, 721*c*, 721*d*, 721*e*, 721*f*, the control module 830 can automatically deliver digital information received from the control unit 714 to the Nth data processing module 844.

The circuit 805 can comprise a front-end processing module 831, which can function similarly to a front-end submodule (not shown) of the control module 230 of the system 100. In particular, the front-end processing module 831 can be configured to condition an analog signal received from the sensor 716 and/or convert the analog signal into a digital signal. The front-end processing module 831 can comprise any suitable components for processing and/or converting the signal, such as one or more filters (not shown), amplifiers 832, and/or analog-to-digital converters 834. Operational frequencies, gains, sampling rates, or other parameters of the components of the front-end processing module 831 can be tailored to a particular patient parameter, as known in the art. Additionally, checksums or forward correction may be used with the converted digital information, as know in the art. Although the microcontroller 820 and the front-end processing module 831 are depicted as separate components in the illustrated embodiment, in some embodiments, the microcontroller 820 can in include the circuitry of the front-end processing module 831.

In use, the sensor 716 of the illustrated embodiment generates analog signals representative of a patient parameter. The analog signals are delivered to the front-end processing module 831 and are converted to digital signals that may be representative of the analog signals. The digital signals are delivered to the control module 830 of the display unit 710, and are then routed to one of the processing modules 840, 842, 844. In some embodiments, the data processing module 840, 842, 844 can convert the digital signal, or a portion thereof, back into an analog signal (such as, for example, a waveform) for display on the screen 728.

Figure 11:
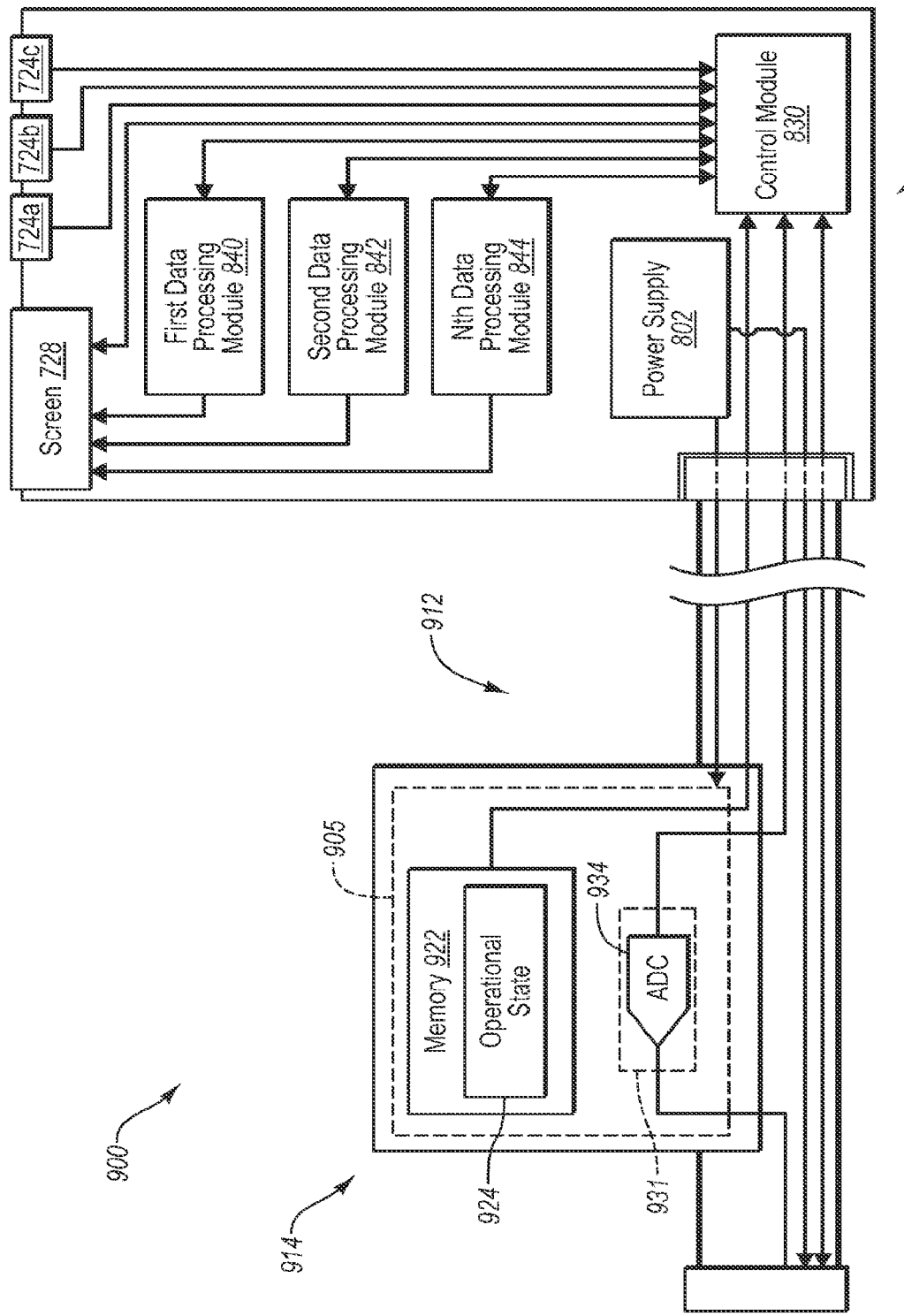
FIG. 11 is a simplified block diagram schematically illustrating other embodiments of a monitor and a control unit in a coupled state.

FIG. 11 illustrates an embodiment of a system 900 that includes the patient monitor 710 and another embodiment of a cable 912, which can include an embodiment of a control unit 914. The cable 912 and the control unit 914 can resemble the cables 711, 712 and the control unit 714, respectively, thus like features are represented by like reference numerals, with the leading digit incremented to "9." However, unlike the embodiment of the control unit 714 depicted in FIG. 10, the control unit 914 does not include actuators or a display screen. Rather, a memory device 922 stores a single operational state 924 of a circuit 905. Upon connection of the cable 912 to the patient monitor 710, the control module 830 can automatically detect the operational state of the circuit 905 and can route information received from the cable 912 to the appropriate data processing module 840, 842, 844. Stated otherwise, the cable 912 can be dedicated for use in monitoring a specific patient parameter, and the control module can detect which patient parameter this is and respond accordingly. The control unit 914 can include a front-end processing module 931 that includes an analog-to-digital converter 934.

Figure 12:
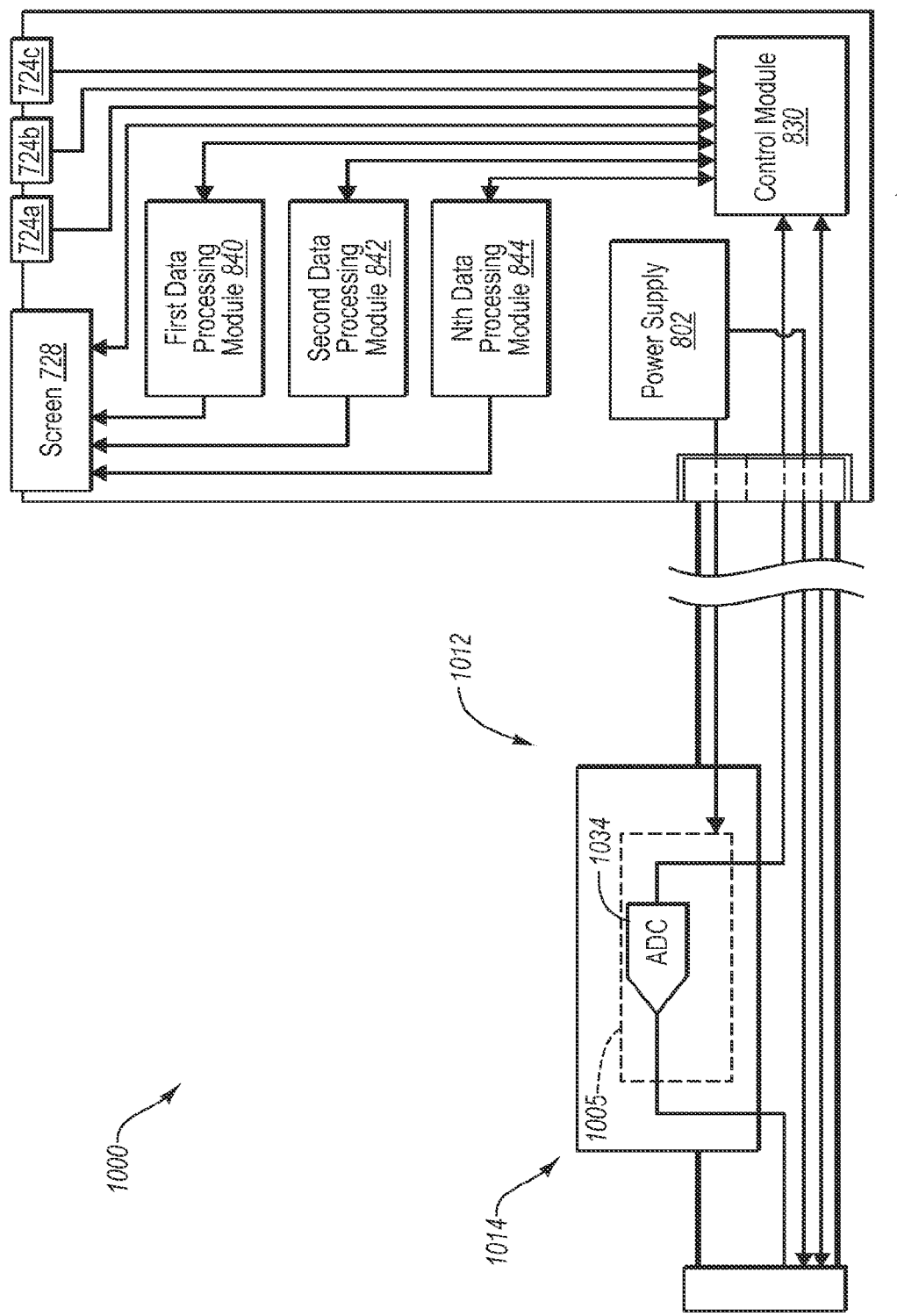
FIG. 12 is a simplified block diagram schematically illustrating other embodiments of a monitor and a control unit in a coupled state.

FIG. 12 illustrates an embodiment of a system 1000 that includes the patient monitor 710 and another embodiment of a cable 1012, which can include an embodiment of a control unit 1014. The cable 1012 can resemble the cables 711, 712, 912, and the control unit 1014 can include a circuit 1005 having an analog-to-digital converter 1034. Unlike the embodiment of the control unit 914 depicted in FIG. 11, however, the control unit 1014 does not include a memory device that stores an operational state of the circuit. Accordingly, in some embodiments, rather than the patient monitor 710 automatically selecting which data processing module 840, 842, 844 to use in processing digital information received from the control unit 1014, a user may select the appropriate module 840, 842, 844 via one or more of the actuators 724a, 724b, 724c of the patient monitor 710.

Figure 13:
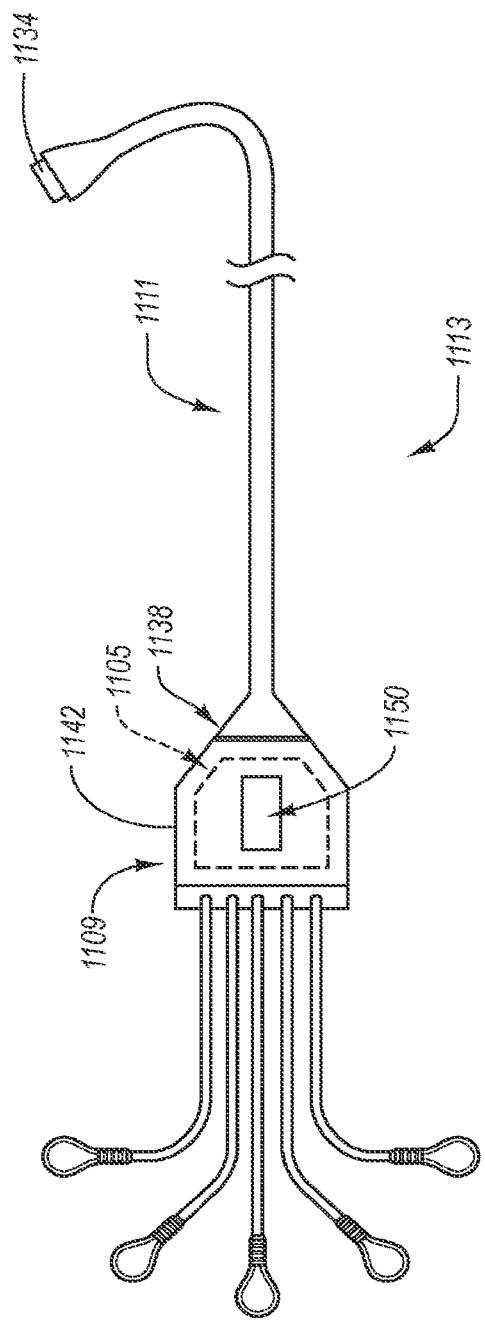
FIG. 13 is a perspective view of an embodiment of an information delivery system compatible with embodiments of patient monitoring systems disclosed herein.

FIG. 13 illustrates an embodiment of an information delivery system 1113 such as the information delivery system 713 discussed above. Like features are represented by like reference numerals, with the leading digits incremented to "11." The system 1113 is dedicated for use in electrocardiography, and may include a circuit 1105 having a single operational state (similar to the circuit 905 discussed above). In particular, the system 1113 can include a yoke 1109, which can include a housing 1142. The housing can substantially enclose or encase the circuit 1105.

In the illustrated embodiment, the circuit 1105 is coupled with a display 1150, which can indicate such information as the status of the cable, whether any faults are present in the leads, etc. The information delivery system 1113 can include a cable 1111 having a proximal connector 1134 and a distal connector 1138. In the illustrated embodiment, the distal connector 1138 is physically coupled directly to the housing 1142.

It will be understood by those having skill in the art that many changes may be made to the details of the above-described embodiments without departing from the underlying principles of the present invention. The scope of the present invention should, therefore, be determined only by the following claims. Recitation in the claims of the term "either" does not necessarily refer to two exclusive options, and may include within its scope more options than those explicitly listed. Recitation in the claims of the term "first" with respect to a feature or element does not necessarily imply the existence of a second or additional such feature or element.

What is claimed is:

1. A patient monitoring system comprising:
 a patient monitor configured to display information regarding a patient, wherein the patient monitor comprises a first port and a first wireless communicator;
 a cable comprising a proximal end and a distal end, and further comprising:
  a cable body that extends between the proximal and distal ends, wherein the proximal end of the cable comprises a first connector configured to electrically couple the cable body with the first port of the patient monitor;
  wherein the distal end comprises a connector comprising a distal interface configured to selectively couple with a patient parameter sensor and receive analog signals from the patient parameter sensor; and
 a first circuit, the first circuit comprising a front-end processing module configured to condition the analog signals from the patient parameter sensor and convert the analog signals into digital signals, wherein the first circuit is external to the patient monitor, wherein the first circuit comprises a second wireless communicator to wirelessly communicate the digital signals to the patient monitor, and wherein the first circuit is at a distance of no less than about 3.0 feet from the distal interface along a length of the cable body to limit a distance over which the analog signal is transmitted over the cable;
 wherein the cable body comprises one or more power leads that are configured to provide electrical power from the first port of the patient monitor to one or more of the distal interface and the first circuit.

2. The system of claim 1, wherein the patient monitor is configured to process digital information received from the first circuit in any of two or more operational modes, wherein the first circuit is configured to communicate an operational state of the first circuit to the patient monitor, and wherein the patient monitor is configured to automatically process said digital information received from the first circuit in an operational mode that corresponds with the communicated operational state of the first circuit.

3. The system of claim 2, wherein the first circuit is configured to transition among two or more operational states, and wherein each of said operational states corresponds with an operational mode of the patient monitor.

4. The system of claim 3, wherein the cable further comprises an actuator electrically coupled with the first circuit, wherein the actuator is configured to transition the first circuit among the two or more operational states.

5. The system of claim 3, further comprising a display external to the patient monitor configured to provide a visually perceivable representation of a current operational state of the first circuit.

6. A system configured to provide digital signals to a patient monitor, the system comprising:
 a cable comprising a proximal end and a distal end, and further comprising:
  a cable body that extends between the proximal and distal ends, wherein the proximal end of the cable comprises a first connector configured to electrically couple the cable body with the first port of the patient monitor;
  a distal electrical interface at the distal end configured to receive analog signals from a patient parameter sensor; and
  a circuit, wherein the circuit is configured to condition the analog signals from the patient parameter sensor and convert the analog signals into digital signals, and wherein the circuit comprises a wireless communicator to wirelessly communicate the digital signals to a patient monitor to limit a distance over which the analog signal is transmitted over the cable;
  wherein the cable body comprises one or more power leads that are configured to provide electrical power from the first port of the patient monitor to one or more of the distal interface and the first circuit.

7. The system of claim 6, wherein the first circuit is at a distance of no more than about 3.0 feet from the distal end along a length of the cable.

8. The system of claim 6, wherein the circuit is within a housing that defines a volume of no more than about 5.0 cubic inches.

9. The system of claim 6, wherein the circuit is integral with the cable.

10. The system of claim 6, further comprising an actuator electrically coupled with the circuit, wherein the actuator is configured to transition the circuit among two or more operational states.

11. The system of claim 10, further comprising a display electrically coupled with the circuit, wherein actuation of the actuator is configured to alter information depicted via the display.

12. The system of claim 6, further comprising an actuator electrically coupled with the circuit, wherein actuation of the actuator is configured to effect one or more of zeroing of a patient parameter sensor when the sensor is coupled with the distal electrical interface, instigation of a measurement of blood pressure via a noninvasive blood pressure sensor when the sensor is coupled with the electrical interface, instigation of a diagnostic check of the cable, access of information stored in a memory portion of the circuit, alteration of information stored in a memory portion of the circuit, erasure of information stored in a memory portion of the circuit, and storage of information in a memory portion of the circuit.

13. The system of claim 6, further comprising a patient parameter sensor coupled with the distal electrical interface.

14. The system of claim 13, wherein the cable comprises the circuit.

15. A system configured to provide signals to a patient monitor, the system comprising:
   a cable comprising a proximal end and a distal end, and further comprising a cable body that extends between the proximal and distal ends;
   a distal electrical interface at the distal end configured to receive signals from a patient parameter sensor;
   a circuit in communication with the proximal electrical interface, wherein the circuit is configured to condition the analog signals from the patient parameter sensor and convert the analog signals into digital signals and to wirelessly transmit the digital signals to a patient monitor; and
   an actuator electrically coupled with the circuit, wherein the actuator is configured to allow selection of an operational state of the circuit corresponding to a type of patient parameter sensor;
   wherein the cable body comprises one or more power leads that are configured to provide electrical power from the patient monitor to one or more of the distal interface and the first circuit.

16. The system of claim 15, wherein actuation of the actuator is configured to effect one or more of zeroing of a patient parameter sensor when the sensor is coupled with the electrical interface, instigation of a measurement of blood pressure via a noninvasive blood pressure sensor when the sensor is coupled with the electrical interface, instigation of a diagnostic check of the cable, access of information stored in a memory portion of the circuit, alteration of information stored in a memory portion of the circuit, erasure of information stored in a memory portion of the circuit, and storage of information in a memory portion of the circuit.

17. The system of claim 15, wherein the actuator is no further than about 3.0 feet from the distal end of the cable when the system is in an assembled state and the cable is fully extended.

18. A method of communicating a signal to a patient monitor, the method comprising:
   providing a cable having a distal end coupled with a patient parameter sensor and a proximal end configured to electrically couple with a first port of the patient monitor, wherein the cable comprises a circuit and an actuator;
   receiving an indication of an operational state of the circuit via the actuator;
   obtaining an analog signal via the patient parameter sensor;
   conditioning and converting the analog signal to a digital signal, using the circuit, according to the operational state of the circuit; and
   wirelessly transmitting the digital signal to the patient monitor to limit a distance over which the analog signal is transmitted over the cable, wherein the cable comprises one or more power leads that are configured to provide electrical power from the first port of the patient monitor to one or more of the patient parameter sensor and the first circuit.

19. The method of claim 18, wherein conditioning and converting the analog signal to a digital signal comprises conditioning and converting using a circuit that is positioned no more than about 3.0 feet from the distal end along a length of the cable.

* * * * *